United States Patent [19]

Nischwitz et al.

[11] 4,096,289
[45] Jun. 20, 1978

[54] ELECTROSTATIC DEPOSITION OF SWELLABLE, MODIFIED CELLULOSE ETHER ON WATER WET HYDROPHILIC SUBSTRATE

[75] Inventors: Ehrenfried Nischwitz, Schmitten; Klaus Uhl, Neuenhain; Helmut Lask, Wiesbaden, all of Germany

[73] Assignee: Hoechst Aktiengesellschaft, Germany

[21] Appl. No.: 750,433

[22] Filed: Dec. 14, 1976

[30] Foreign Application Priority Data

Dec. 17, 1975 Germany .............................. 2556723

[51] Int. Cl.² .......................... B05D 1/06; B05D 3/00; B05D 5/04
[52] U.S. Cl. ....................................... 427/32; 118/629; 128/290 R; 427/324; 427/424; 428/297
[58] Field of Search ....................... 427/27, 52, 14, 25, 427/200, 206, 180; 428/90, 326, 297, 393, 532, 537; 128/290 R, 290 P, DIG. 8; 162/192; 239/3, 15; 118/629-635

[56] References Cited

U.S. PATENT DOCUMENTS

| | | | |
|---|---|---|---|
| 2,889,805 | 6/1959 | Freeder | 118/602 X |
| 3,589,364 | 6/1971 | Vean et al. | 162/146 X |
| 3,661,154 | 5/1972 | Torr | 128/284 |
| 3,901,236 | 8/1975 | Assarsson et al. | 128/290 R |

*Primary Examiner*—Morris Kaplan
*Attorney, Agent, or Firm*—James E. Bryan

[57] ABSTRACT

Process for the transformation of comminuted and modified cellulose ether swellable with water, into a material that may easily be further processed and may thus be used without difficulty in particular in the production of hygienic pads, napkins, bandages, tampons, wrapping papers, insulating material, household papers and similar articles. In said process the modified cellulose ether is attached by electrostatic flocking to at least one surface of a web-shaped hydrophilic support that has been wetted with water and the support is dried.

3 Claims, 4 Drawing Figures

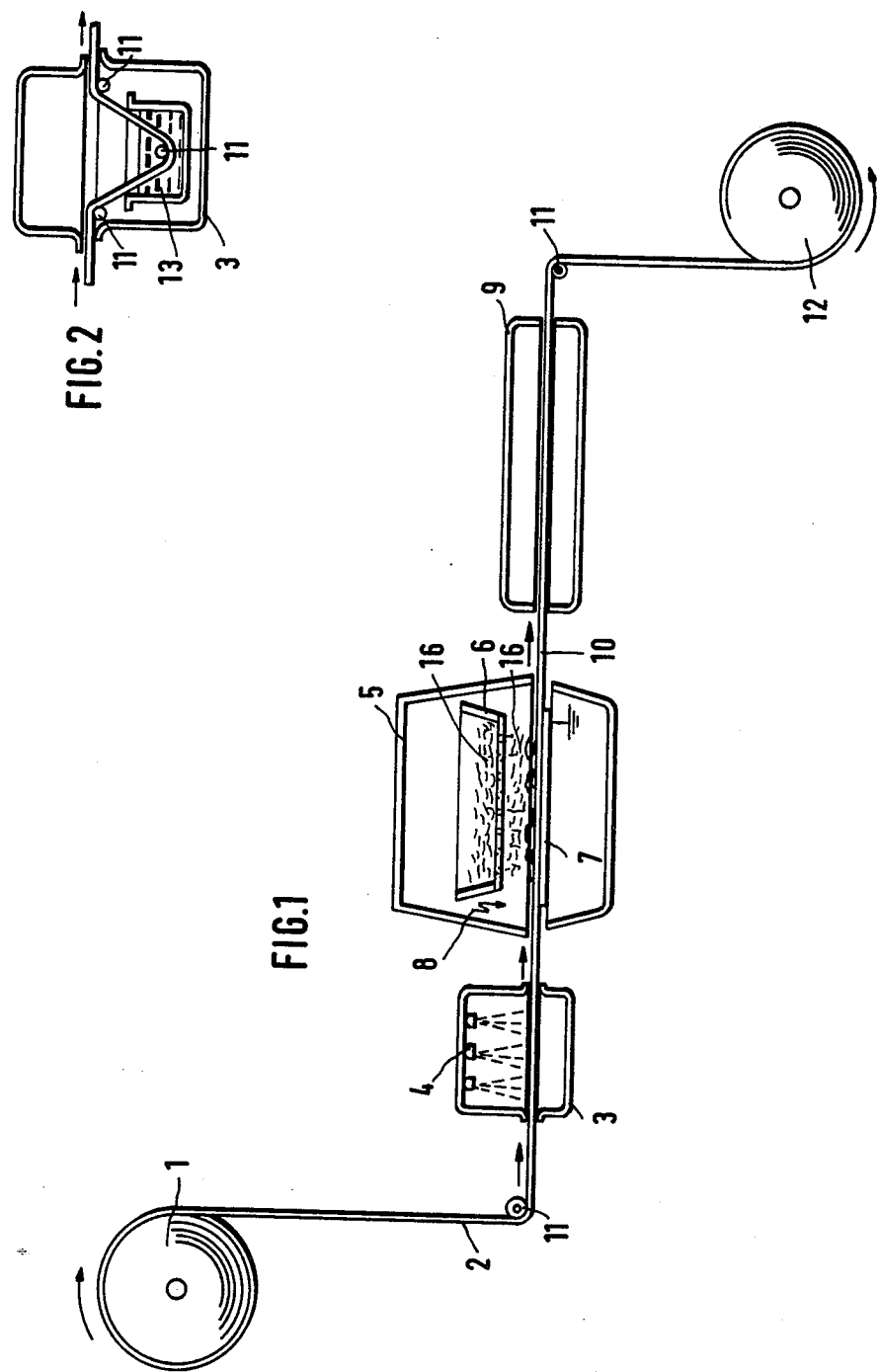

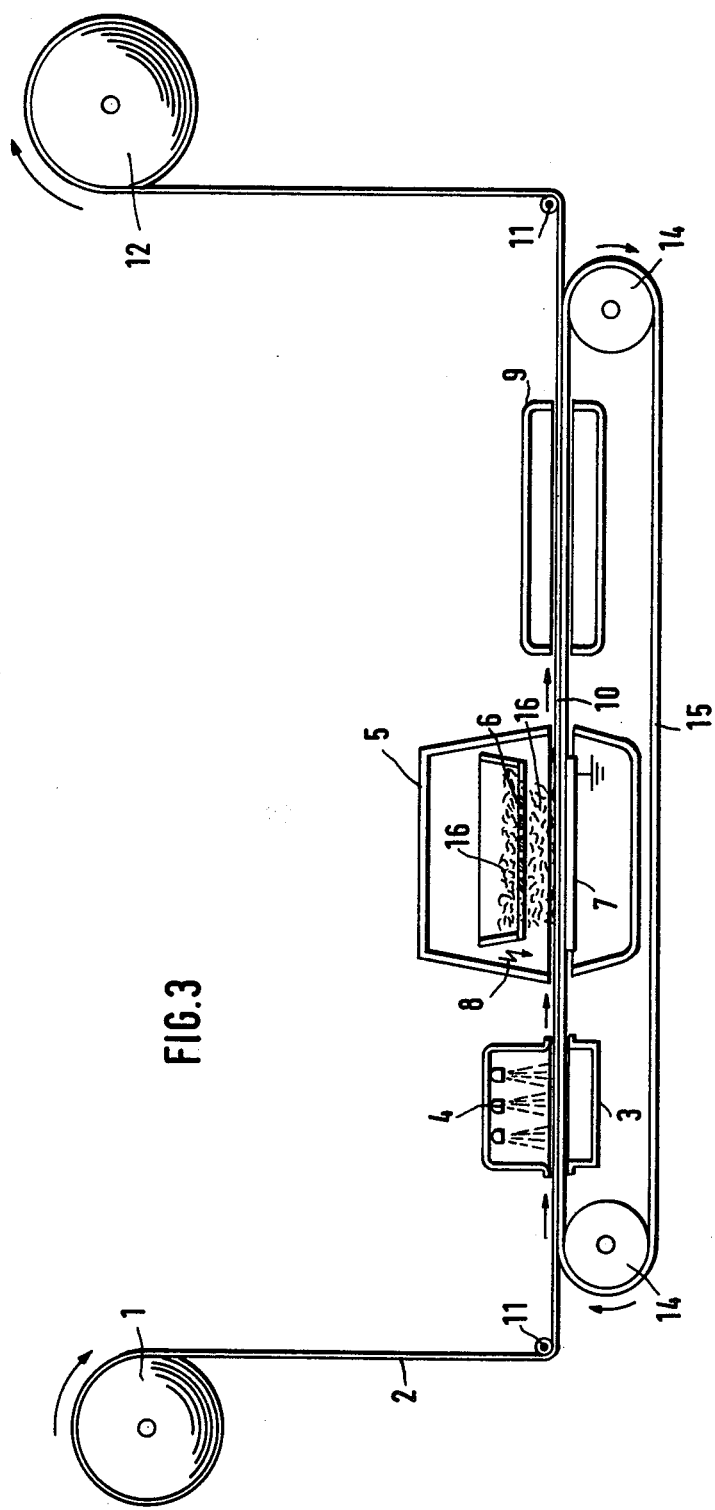

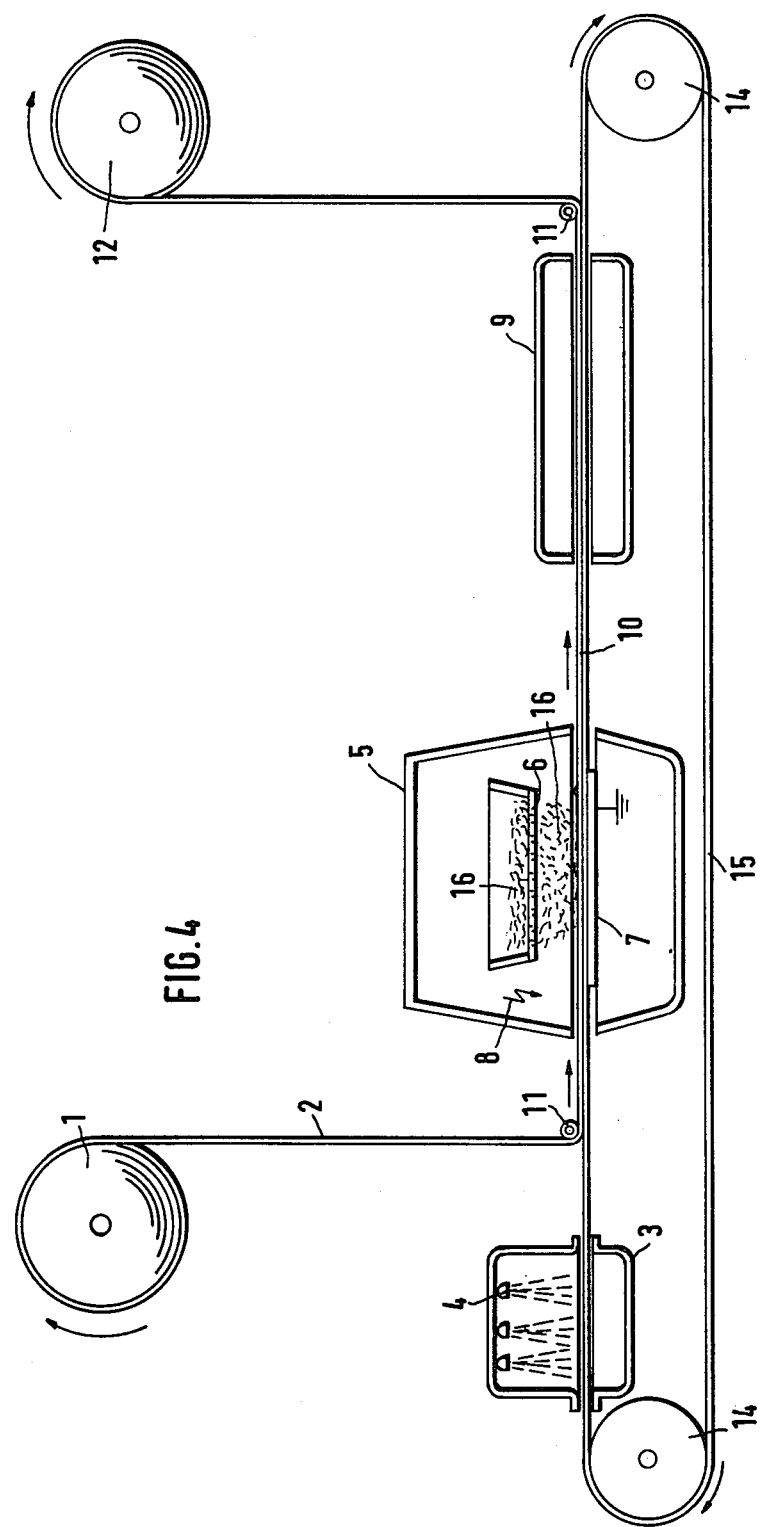

ELECTROSTATIC DEPOSITION OF SWELLABLE, MODIFIED CELLULOSE ETHER ON WATER WET HYDROPHILIC SUBSTRATE

The present invention relates to a process for the transformation of comminuted and modified cellulose ether swellable with water, into a material that may easily be further processed and may thus be used without difficulty in particular in the production of hygienic pads, napkins, bandages, tampons, wrapping papers, insulating material, household papers and similar articles.

For the manufacture of such products tissues or fleeces are used that can absorb aqueous liquids, in particular physiological body fluids such as blood or urine. In our copending application Ser. No. 709,269 a coated web composed of a hydrophilic material is described at least one surface of which is provided with a comminuted modified cellulose ether which is used for improving the absorption capacity of such products. In the same application a process for the production of these coated webs is claimed, i.e. a process for the transformation of comminuted cellulose ether, which has been rendered at least largely water-insoluble by modification but has remained highly swellable with water, into an easily usable material. This process is characterized in that the comminuted and modified cellulose ether is attached to a web-shaped hydrophilic support, at least one surface of the web is wetted with water, the wetted surface is covered with comminuted and modified cellulose ether and the web is dried.

It is the object of the present invention to provide a different process that can be carried out with little technical expenditure. The process according to the present invention is characterized in that the modified cellulose ether is attached to the support by means of electrostatic flocking.

The modified cellulose ethers usable in the process may have any form as long as they are comminuted and electrostatically flockable. Those cellulose ethers are preferably used that have been modified by cross-linking according to the process described in German Offenlegungsschrift No. 2,357,079 or have been modified according to the process disclosed in German Offenlegungsschrift No. 2,358,150. They have high water absorption and water retention values. Modified cellulose ethers usable within the scope of the invention are also, for example, those mentioned in German Patent Applications Nos. P 25 20 336.5, P 25 20 337.6, P 25 19 927.3 and P 25 43 187.2, in German Pat. No. 839,492 and U.S. Pat Nos. 3,589,364, 3,723,413 and 2,639,239. These modifications of cellulose ethers lead to products having an acceptable water absorption capacity even if the modified cellulose ether still contains water-soluble parts. Thus in practice cellulose ethers are often not modified to form completely water-insoluble products, and moreover it is not necessary to remove the soluble parts. The soluble portion usually consists of cellulose ether molecules that are either not modified at all or not enough. The compounds mentioned above are often in a fibrous or pulverized state so that it is possible to transform them into flat-shaped articles, for example by suspending them in a wet process similar to that of paper production. The flat-shaped articles that can be produced in this manner have a rigidity similar to that of paper and are brittle, so that they can hardly be used in the hygienic field, e.g. in napkins or tampons.

In German Offenlegungsschrift No. 24 41 781 it has also been disclosed to fix modified cellulose ethers on textile areas by means of binders.

The flat-shaped articles produced in this manner do have an increased absorption capacity towards liquids, however, it is low relative to the quantity of cellulose ether used, because the binder makes a portion of it ineffective. Furthermore, in this method the portion of binder may cause a hardening which is undesired, especially if the products are to be used as hygienic articles.

However, if the material is produced according to the process of the invention the disadvantages mentioned above do not occur. In this case the web-shaped support is, for example, a tissue, knit fabric, fleece or especially paper compressed of cellulose, wood pu;p, synthetic fibres or a mixture of them, and has certain absorption and retention capacities towards liquids. The weight of this material is between 12 and 500 g/m$^2$.

The drawing shows diagrammatically:

in FIG. 1 an apparatus for performing the invention process, in particular comprising a device 3 for applying water to the surface of a web-shaped support 2, a device 5 for electrostatic flocking and a device 9 for drying the flocked support 10.

in FIG. 2 an embodiment of the device 3 for applying water, comprising a dip tank 13;

in FIG. 3 an apparatus for performing the inventive process according to FIG. 1 with an additional moving endless belt 15 on which the support rests;

in FIG. 4 an apparatus for performing the inventive process according to FIG. 3 in which the endless belt, at the same time, serves as a device for applying water to the surface of the web-shaped support.

The electrostatic flocking and thus coating of the support 2 is effected according to FIG. 1 by wetting at least one of its surfaces with water, for example by dipping (see FIG. 2), spraying 4 or impregnating (see FIG. 2) and guiding the still wet material through a high-voltage field of up to 100 kv, preferably about 30 to 60 kv. One (6) of the two electrodes 6,7 which produce the high-voltage field has the shape of a screen or a perforated plate and serves the purpose of housing the modified cellulose ether 16, which preferably consists of very short fibres having a length of from about 0.05 to 1mm, advantageously about 0.05 to 0.3 mm, and does not require any particular preparation of the fibre or any antistatic aids. The width of mesh or the diameter of one perforation of the electrode is determined such that it is 60 to 100 times the diameter of the cellulose ether fibre. The counter-electrode 7 is flat-shaped, and within the area 5 of the high-voltage field it is not confined to its electrostatic use, but also serves, for example, as a support for the material to be flocked that is guided between the two electrodes 6,7 in such a manner that it is at a distance of about 10 to 50 cm from the perforated or screen electrode 6 and is close to the counter-electrode 7.

After having passed through the electric field the flocked material 10 is dried, for example by a heat radiator or in a heating chamber 9 and may then be wound up 12.

The rollers 11 serve to effect a reversal of the transport direction of the web.

In the case of material having a low wet strength, like tissue paper for example, an endless belt 15 able to support load may be used as an additional support (see FIG. 3) between the storage roller 1 and the wind-up roller 12, a belt which consists essentially of a plastics film, a plastic grate or a metal net and which is moved by a transport mechanism 14. This device is advantageously arranged in the area of the apparatus through which the wet material passes, i.e. the area between the wetting (3) and drying (9) areas.

In another embodiment (see FIG. 4) of the process according to the invention, which is preferably applied in the electrostatic flocking of material such as creped paper in order to maintain its original shape, e.g. the crepe, first an endless belt 15 is wetted 3,4 which then in turn wets the material 2 to be flocked that comes into contact with the belt. Flocking (5) and drying (9) are carried out as described above.

The material to be flocked onto the support, which consists of modified cellulose ether 16, is advantageously kept in motion by mechanical means, e.g. by a slight vibration or a revolving scraper, in order to avoid bridge-forming between its particles in the electrode, because this may impair the mobility of the flocks.

The cellulose ether particles 16 are pushed from the screen electrode 6 in the direction of the counter-electrode 7 and thus also in the direction of the web-shaped support 2 between the electrodes. They absorb water from the wet surface of the support and swell. The swelling prevents a possible return of the particles, which may be caused, for example, by charge reversion, and thus the support is uniformly covered with modified cellulose ether. It is expected that during the drying (9) that follows the swollen particles are glued to the support, thus ensuring good adherence and preventing the particles detaching themselves in the form of dust.

The process according to the invention may be carried out continouosly as well as discontinuously, the density of the coating on the support being widely variable. It depends, for example, on the quantity of water applied, on the voltage 8 applied to the electrodes 6,7, but also on the particle size of the modified cellulose ether 16 to be flocked. The density may be up to 100 g/m$^2$, in the case of material to be used for hygienic purposes it preferably is 15 to 30 g/m$^2$.

All the web-shaped materials produced according to the process of the invention are highly absorbent and have a high liquid retention capacity. Since they are also easily workable it is advantageous to include them as a bottom, intermediate or top layer in flat-shaped laminar articles as they are used, for example, in the hygienic field in bandages, napkins or bed sheets, in order to improve their absorption capacity. The material produced according to the invention may also be used as intermediate layer in flat-shaped articles having a "sandwich structure", for example, dish-cloths, oil-absorbing mats and the like.

EXAMPLE 1

A creped paper having a weight of 25 g/m$^2$ and a width of 30 cm is unwound from a supply roller and is applied without pressure to an endless polyester film that has a width of 40 cm, moves at a speed of 80 m/min and is continuously sprayed with water. The film and the paper thus wetted are guided through a 50 kv high-voltage field. One electrode has the form of a screen and is filled with carboxymethyl cellulose modified with the cross-linking agent dimethylol methylene bisacrylamide and having an average fibre-length of 0.1 mm. The screen electrode is arranged at a distance of 25 cm from the paper. After the flocking the material passes through the area of an infrared radiator for drying and can then be wound up. The quantity of modified cellulose ether applied is 25 g/m$^2$.

EXAMPLE 2

A cotton-nettle cloth tissue having a weight of 150 to 170 g/m$^2$ and a width of 50 cm is unrolled from a supply roller at a speed of 20 m/min, is wetted with water with the aid of a spray tube and then is guided through a 60 kv high voltage field. The screen electrode is arranged at a distance of 35 cm from the paper and is filled with a carboxymethyl cellulose modified with N-methylol acrylamide, having an average fibre length of 0.2 mm. The quantity of modified cellulose ether flocked onto the material and still present there after drying is 18 g/m$^2$. The dried material can be wound up.

What is claimed is:

1. A process for the transformation of comminuted cellulose ether, which has been rendered at least largely water-insoluble by modification but has remained highly swellable with water, into an easily usable material, a process in which the modified cellulose ether is attached to at least one surface of a web-shaped hydrophilic support that has been wetted with water and the support is dried, the process comprising the modified cellulose ether attached to the support by electrostatic flocking.

2. A process according to claim 1, in which the modified cellulose ether is used in the form of fibres having an average length of 0.05 to 1 mm, preferably 0.05 to 0.3 mm.

3. A process according to claim 1, in which the quantity of cellulose ether attached to the support is up to 100 g/m$^2$, preferably about 15 to 30 g/m$^2$.

* * * * *